Figure 1:
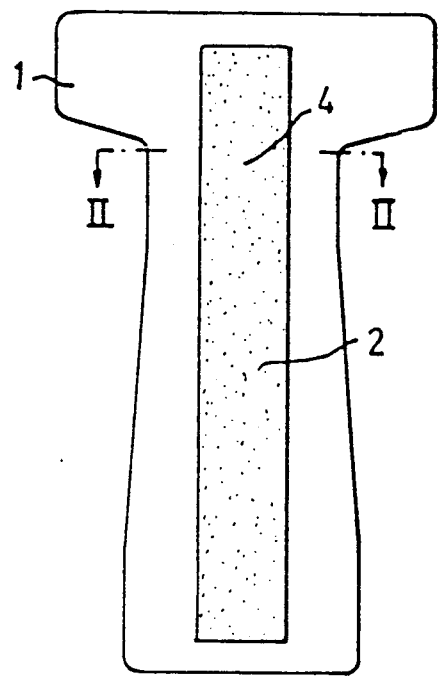

United States Patent [19]

Ternström

[11] Patent Number: 5,043,206

[45] Date of Patent: Aug. 27, 1991

[54] ABSORPTION BODY INTENDED FOR DISPOSABLE ARTICLES SUCH AS DIAPERS, SANITARY NAPKINS AND THE LIKE

[75] Inventor: Ingela Ternström, Mölnlycke, Sweden

[73] Assignee: Molnlycke AB, Goteborg, Sweden

[21] Appl. No.: 886,097

[22] Filed: Jul. 16, 1986

[30] Foreign Application Priority Data

Jul. 31, 1985 [JP] Japan .............................. 60-169629

[51] Int. Cl.⁵ .............................................. B32B 7/02
[52] U.S. Cl. ................................... 428/218; 428/280; 428/281; 428/283; 428/284; 428/402; 428/913; 428/326; 604/367; 604/379
[58] Field of Search .............. 428/913, 284, 326, 218, 428/219, 280, 281, 363, 283, 402; 604/367, 368, 379

[56] References Cited

U.S. PATENT DOCUMENTS

| 3,661,154 | 5/1972 | Torr ..................... 128/284 |
| 3,837,343 | 9/1974 | Mesek .................. 128/287 |
| 4,055,180 | 10/1977 | Karami ................ 128/287 |
| 4,102,340 | 7/1978 | Mesek et al. ........ 128/287 |
| 4,354,901 | 10/1982 | Kopolow ............. 162/158 |
| 4,381,783 | 5/1983 | Elias .................... 604/368 |
| 4,573,988 | 3/1986 | Peniak et al. ....... 604/379 |
| 4,604,313 | 8/1986 | McFarland et al. ... 428/172 |
| 4,676,784 | 6/1987 | Erdmann et al. .... 604/368 |
| 4,685,915 | 8/1987 | Hasse et al. ........ 604/378 |
| 4,699,823 | 10/1987 | Kellenberger et al. ... 428/218 |

FOREIGN PATENT DOCUMENTS

| 0158914 | 10/1985 | European Pat. Off. |
| 1403603 | 8/1975 | United Kingdom |
| 2087240 | 5/1982 | United Kingdom |
| 2131699 | 6/1984 | United Kingdom |
| 2144995 | 3/1985 | United Kingdom |
| 2151488 | 7/1985 | United Kingdom |

Primary Examiner—James J. Bell
Attorney, Agent, or Firm—Young & Thompson

[57] ABSTRACT

An absorption body intended for disposable articles such as diapers, sanitary napkins or the like and comprising highly absorbent material. A distinguishing feature of an absorption body made in accordance with the invention is that there is included therein a first layer intended to be placed against the wearer's body and which is soft, with a bulk exceeding 10 cm³/g, preferably more than 13 cm³/g, and at least one second layer which is heavily compressed to a bulk of less than 10 cm³/g; and that the highly absorbent material is applied in the heavily compressed layer or layers.

5 Claims, 1 Drawing Sheet

ABSORPTION BODY INTENDED FOR DISPOSABLE ARTICLES SUCH AS DIAPERS, SANITARY NAPKINS AND THE LIKE

The present invention relates to an absorption body intended for disposable articles such as diapers, sanitary napkins and the like, and containing highly absorbent material.

Although absorption bodies containing highly absorbent material are known per se, there has so far existed no method, which function well in all respects, of fixing the highly absorbent material in absorption bodies consisting otherwise of absorbent cellulose fluff pulp.

Such prior art absorption bodies of cellulose have low density and poor strength, which means that it has been impossible to satisfactorily bind a highly absorbent material, especially in powder form, in the absorption body. Consequently, the powder is substantially freely movable in these known absorption bodies and may be collected where undesired in diapers, for example, as a result of the infant's movements, thereby negatively influencing the distribution of liquid in the absorption body.

The problem is due to the fact that the highly absorbent material, which has a very high liquid-retaining capacity, almost completely lacks a liquid-distributing capacity. As a consequence, liquid reaching a collection of highly absorbent material will not be spread therein but is instead transported around the accumulated material.

In case a material in powder form is used, each single grain must therefore be fixed at mutually spaced points, and the rest of the absorption body must posses a satisfactory liquid-transmitting capacity in order to fully utilize the liquid-absorbing capacity of the powder.

Since no successful method of fixing highly absorbent powder is an absorbent core has been found so far, there has instead been suggested the application of thin layers of tissue, for example, onto which the powder is fixed with the aid of a binder. There has further been suggested the application of individual powder grains in separate pockets between two thin layers of fiber fabric, for example.

These known methods, however, involve the drawback that the highly absorbent powder be located in one single plane, and therefore the quantity of powder will be insufficient for increasing to any appreciable extent the liquid-absorbing capacity of the absorption body.

With the present invention, the problem of fixing highly absorbent powder in cellulose absorption bodes has now been solved.

An absorption body made in accordance with the invention is primarily distinguished in that it comprises a first layer which is intended to be placed against the wearer's body, and which is soft and has a bulk exceeding 10 cm$^3$/g, preferably more than 13 cm$^3$/g, and at least one second layer which has a substantially higher degree of compression and a bulk of less than 10 cm$^3$/g, preferably between 4 and 8 cm$^3$/g; and in that the highly absorbent material is applied in the absorption body underneath the first layer in one or more of said heavily compressed layers.

Absorption bodies according to the invention, compressed to such a high density as in the second layer, will substantially retain their stable shape even during use of the absorption body, for example in a diaper. In this manner the heavily compressed layers will be stable enough for the individual, highly absorbent powder grains to be fixed in position in the absorption body.

Figure 2:
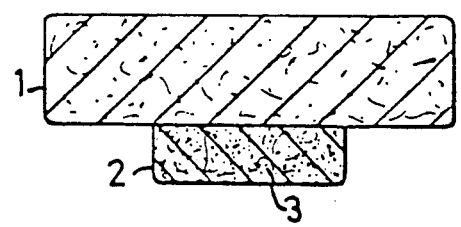

The invention will be described more closely in the following, with reference to an exemplary embodiment illustrated in the drawing, wherein FIG. 1 is a plan view of an absorption body according to the invention, intended for use in disposable diapers, and FIG. 2 shows to a larger scale a cross section taken along the line II—II in FIG. 1.

The absorption body illustrated in FIG. 1 consists of a substantially T-shaped first layer 1 of cellulose fluff pulp. The widened portion of the first layer 1 is intended for application against the wearer's abdomen while preventing the diaper from slipping backwards upon movements of the wearer. The layer 1, which is soft and has a bulk of more than 10 cm$^3$/g, preferably more than 13 cm$^3$/g, is intended to be placed closest to the wearer's body during use. The absorption body further includes a rectangular layer 2 which is heavily compressed and has a bulk of less than 10 cm$^3$/g, preferably between 4 and 8 cm$^3$/g. Advantageously, the two layers 1,2 are bonded together by means of hot melt, for example. Both of the absorption layers are air-laid and compressed to the above-mentioned bulk values. At the time of the second layer 2 being air-laid, a highly absorbent powder 3 such as that marketed under the trade name SANWET by the Japanese company Sanyo, is mixed with the fluff pulp.

The heavily compressed second layer 2 has a width fitting the wearer's crotch and is situated underneath the layer 1 during use of the diaper.

The absorption body is intended to be enclosed in a casing (not shown) for creating a diaper to be discarded after a single use. In general, such a casing consists of a liquid-permeable outer layer applied to the first layer 1, and a liquid-impermeable outer layer applied to the opposite side of the absorption body. The two outer layers extend outside the absorption body, where they are united.

When using the described and illustrated absorption body in a diaper, the soft layer 1 is first wetting at the so-called wetting point, designated by 4 in FIG. 1. Due to the poor liquid-distributing capacity of the soft layer 1, discharged urine will substantially fall right through this layer and down into the underlying, heavily compressed second layer 2. Owing to the extremely large liquid-transporting capacity of this layer, the urine will be rapidly distributed all through said layer, despite the action of gravity. The highly absorbent powder 3, which is spread all over the second layer 2 and is fixed in position by means of the high compression, can now be fully utilized while giving the second layer 2 an exceptional liquid-retaining capacity.

The invention is not restricted to the exemplary embodiment described above, but a plurality of modifications are feasible within the scope of the claims.

The absorbent core illustrated in the exemplary embodiment can either constitute a part of a so-called complete disposable diaper, i.e. a diaper where the casing wrapped around the absorption body is designed as a pant-shaped unit, or it can be used in combination with a separate, elastic co-called baby pant.

I claim:

1. An absorption body for disposable articles such as diapers, sanitary napkins and the like, comprising a first layer of cellulose fluff pulp which is adapted to be placed against the wearer's body and which is soft and has a bulk density exceeding 10 cm$^3$/g and which thereby has a poor liquid-distributing capacity, at least one air-laid second layer of cellulose fluff pulp which is substantially more heavily compressed than said first layer and has a bulk density of less than 10 cm$^3$/g and which thereby has a substantially higher liquid-distributing capacity than said first layer, and a highly absorbent powdered material distributed within said at least one second layer during the air-laying of said at least one second layer, said powdered material being fixed in position in said at least one second layer only by the compression of said at least one second layer.

2. An absorption body as claimed in claim 1, in which said bulk of said first layer exceeds 13 cm$^3$/g.

3. An absorption body as claimed in claim 1, in which the bulk of said at least one second layer is between 4 and 8 cm$^3$/g.

4. An absorption body as claimed in claim 1, said first and second layers being bonded together.

5. An absorption body as claimed in claim 1, in which said at least one second layer is an elongated strip of substantially less width than and centered on said first layer.

* * * * *